US005679365A

United States Patent [19]
Henderson et al.

[11] Patent Number: 5,679,365
[45] Date of Patent: Oct. 21, 1997

[54] COMPOSITION AND METHOD FOR FORMING AN INSECTICIDE

[76] Inventors: Dennis Mark Henderson, Rte. 1, Box 275, Caddo Mills, Tex. 74135; Robert Edwin Kluttz, Box 172-10, Rte. 1, Greenville, Tex. 75401

[21] Appl. No.: 284,084

[22] Filed: Aug. 1, 1994

Related U.S. Application Data

[63] Continuation-in-part of Ser. No. 965,896, Oct. 23, 1992, abandoned.

[51] Int. Cl.⁶ .................................................. A01N 25/08
[52] U.S. Cl. ..................... 424/409; 424/406; 424/410; 424/84; 514/918
[58] Field of Search ........................ 424/405, 410, 424/439, 84, DIG. 10, DIG. 11, 485, 488, 195.1, 408, 406, 409; 514/95, 76

[56] References Cited

U.S. PATENT DOCUMENTS

| | | | |
|---|---|---|---|
| 871,612 | 11/1907 | Blumhardt | 424/405 |
| 3,220,921 | 11/1965 | Greenbaum et al. | 167/30 |
| 3,962,461 | 6/1976 | Brown, Jr. et al. | 424/352 |
| 4,460,606 | 7/1984 | Bettarini et al. | 424/341 |
| 4,540,711 | 9/1985 | Bettarini et al. | 514/720 |
| 4,874,611 | 10/1989 | Wilson et al. | 424/410 |
| 4,985,413 | 1/1991 | Kohama et al. | 514/79 |
| 5,094,853 | 3/1992 | Hazarty | 424/405 |
| 5,104,658 | 4/1992 | Hagarty | 424/405 |
| 5,116,618 | 5/1992 | Hagarty | 424/405 |
| 5,126,139 | 6/1992 | Geary | 424/410 |
| 5,141,744 | 8/1992 | Chang et al. | 424/93 |
| 5,152,992 | 10/1992 | Kandathail et al. | 414/405 |
| 5,157,029 | 10/1992 | Casda et al. | 514/150 |

OTHER PUBLICATIONS

Dadd, Nontoxic & Natural : Jams, Jellies & Preserves p. 129, Merck Index 1968 p. 494 Glucose.

*Primary Examiner*—Neil S. Levy
*Attorney, Agent, or Firm*—Jones, Day, Reavis & Pogue

[57] ABSTRACT

A method for preparing and a product made thereby for a bait insecticide composition that is toxic toward fire ants (Solenopsis saevissima v. richterii). Such a composition is comprised of an attractant agent (concord grape extract) mixed with a toxicant (organophosphorous compound) and an enhancing agent (salt). This present invention has the ability to control fire ants while remaining environmentally safe by being inert with regard to most other ants and nearly all other types of insects, rodents and mammals.

36 Claims, No Drawings

COMPOSITION AND METHOD FOR FORMING AN INSECTICIDE

RELATED APPLICATION

This application is a continuation-in-part of U.S. patent application Ser. No. 07/965,896, filed Oct. 23, 1992, abandoned the entire disclosure of which is incorporated herein by reference.

TECHNICAL FIELD OF THE INVENTION

The invention relates in general to a composition and method for forming an insecticide, and more particularly to a composition and method for forming a Solenopsis saevissima v. richterii bait-insecticide.

BACKGROUND OF THE INVENTION

Solenopsis saevissima v. richterii, which are commonly known as fire ants, migrated into the United States from South America during the early 1900's. The rate at which the fire ants have been spreading has increased exponentially; and it has been calculated that in the U.S., fire ants infest with their ant hills (nests) up to 250 per hectare. The infestation into populated regions has caused incalculable problems which have, in the extreme, been fatal.

Prior art has attacked this infestation by using high concentrations of toxic chemicals, which kill a plethora of types of ants, insects, rodents and other species.

The amount of money spent on this problem is sizeable, and there is a noticeable quest for better, more effective pesticides. In fact, there is a wide variety of prior art pesticides that have been unsuccessful in combatting the problem.

For example, U.S. Pat. No. 4,874,611 by Wilson, et al. discloses a method of manufacture and composition of a core including an insect poison encapsulated in a shell material. The shell was resistant to water but could be penetrated by the insect. Because fire ants often have trouble penetrating the shell, this method is not very successful in causing the termination of large numbers of fire ants.

U.S. Pat. No. 3,962,461 by Brown, Jr., et al. discloses a toxic bait for insects, in which the bait contains suspended recrystallized Mirex in a sweet, aqueous solution. This substance is used to combat carpenter ants and is not specifically designed to attract fire ants. Fire ants, in fact, have not been greatly attracted to this bait, resulting in ineffective insecticide for fire ant application.

U.S. Pat. No. 4,460,606 and U.S. Pat. No. 4,540,711 by Bettarini, et al. disclose a method for fighting infestation by fire ants consisting of a bait comprising hydroquinone diether having at least one acetylenic and halogen-substituted chain and selected from 1-[(5-chloro-pent-4-inyl)-oxy]-4 phenoxybenzene and 1,4-di-(5-chloro-4-pentinyloxy)-benzene. Like the Brown pesticide, the Bettarini disclosure has not been successful in reducing fire ant population significantly.

U.S. Pat. No. 3,220,921 by Greenbaum, et al. discloses a poison containing a bait —$C_{10}Cl_{12}$ ($C_5Cl_6$ dimer) composition. This composition eliminates fire ants population; however, this bait also attracted a plethora of other insects (i.e., bees, flies, beetles, etc.). Therefore, this bait has the disadvantages of attracting insects that should not be extinguished because it will upset the ecological balance and eliminates insects, such as honey bees, which are commercially desirable. Furthermore, although this bait attracts fire ants, it does not attract them to the degree necessary to rid large areas of fire ants. Lastly, there appear to be problems with the form of this composition (primarily solid), which makes it difficult to distribute in large quantities over a large geographical area.

U.S. Pat. No. 5,094,853, U.S. Pat. No. 5,104,658 and U.S. Pat. No. 5,116,618 by Hagarty disclose a killing composition containing an organophosphorous compound mixed with a corn sweetener. This composition by Hagarty is a pesticide in the form of an arthropodicidally-active foam matrix. Like the Greenbaum '921 patent composition, this insecticide was designed to control fire ants, as well as certain crustaceans, arachnids, a wide variety of crawling insects and certain myriapods. The problem with this composition, once again, is that it attacks more insects than simply fire ants. Therefore, it too appears to upset the ecological balance more than necessary and kill desirable insects. Furthermore, although this material does attract fire ants, it needs to be spread close to the fire ant hills to be an effective means of control.

None of these toxic compounds have a special affinity toward fire ants. None of these toxic compounds attract fire ants during cold weather. Unlike the present invention, the prior art toxic compositions are consumed by a variety of species and, thus, most cannot be used under circumstances where it is necessary for insects and other species to thrive. The present invention contains an agent which both attracts fire ants and detracts most other ants, insects, rodents and other species from ingesting the toxic compounds. Because most other insects and species will not consume the insecticide, less of the present invention needs to be spread to combat the fire ants. Furthermore, because fire ants appear to purposefully seek out the present invention (even in cold weather), the composition can be dispersed in small quantities throughout the area which needs to be controlled. Therefore, the present invention is more environmentally safe than the prior art.

Lastly, because the present invention can be produced as a liquid or gel and because of its specialized attraction to fire ants, this composition can be spread over a great area with little difficulty, which resultantly reduces the cost to eliminate the same number of fire ants as compared to prior art.

SUMMARY OF THE INVENTION

The present invention provides a method for forming fire ant bait that is normally in the form of a liquid or gel. This composition is comprised of an attracting agent, an enhancing agent, and a toxicant. The primary aspect of the present composition is to combat the infestation of fire ants. The attracting agent comprises a product formed from a liquid extracted from grapes ("grape extract"). One embodiment of the attracting agent comprises a grape jelly in a consistency to readily mix with other additives. The viscosity of the grape jelly can be reduced to the necessary consistency by, for example, heating or beating. Another embodiment of the attracting agent comprising grape juice thickened so that it has a consistency thick enough to keep the liquid from soaking into the ground soon after being spread. The viscosity of the grape juice may be increased by a standard thickening agent.

An enhancing agent is added to the attracting agent to create a composition that appears to be highly attractive to fire ants. The enhancing agent is a salt which reacts with the attracting agent and forms a compound that seems much more appealing to the fire ants than any other attracting agent previously disclosed. For the purposes of this invention, any edible salt may be used.

The addition of salt to the grape jelly and to the grape juice created unforeseen mixtures that each emit a distinct and foul smell. It was unanticipated that this composition would react in this manner and produce a material that seems to deter other types of ants, insects, rodents and mammals and attract the fire ant. Because this enhanced attracting agent emits such a particular odor, it is observed that a greater percent of the present invention enters the fire ant nests. This reduces the amount of composition that needs to be used, compared with other toxic substances, to kill the same number of fire ants.

An organophosphorous compound is added in small quantities to this mixture to make the composition toxic. For example, a suitable toxicant is acetylphosphoramidothiotic acid O,S-dimethyl ester, more commonly called "Acephate," and commercially available under the "Ortho" or "Orthene" brand names. (See also U.S. Pat. Nos. 3,716,600 and 3,845,172, both assigned to Chevron). The present composition is delayed acting, and, therefore, the fire ants will bring the toxic substances back to the ant hills before the insecticide begins to take effect.

The present composition can be in a liquid or gel form, although it can be prepared and then reduced to a solid form. The apparent mechanism of kill is that the fire ants actually ingest the toxic fluid instead of carrying toxic material back to the ant hill. Because literature indicates that fire ants feed from the juices of their dead, the toxic substance is transmitted rapidly throughout the ant community after the infected ants die. Furthermore, the liquid or gel composition appears to stay toxic for a longer period of time than the prior art. Interestingly, the liquid or gel composition maintains its toxicity even after traces of the toxicant can no longer be found in the composition. A major problem suspected with fire ants is that they repopulate old nests. With this apparent longer period of toxicity, the present composition will continue to kill new inhabitants of the nests. Thus, contrary to the majority of other toxic compositions, the composition rids both the present and future generations of fire ants.

DETAILED DESCRIPTION OF THE INVENTION

In accordance with the present invention, a bait-insecticide has been formed that can be used to control the infestation of fire ants. The invention in question comprises a composition of an attracting agent, an enhancing agent, and a toxicant.

The attracting agent comprises a grape extract that may be in the form of a grape jelly, a grape juice, or other similar sweet products. The composition comprising the flavored jelly preferably is at a concentration between approximately 95.0 weight percent and approximately 97.5 weight percent.

One possible embodiment of the attracting agent is grape jelly, preferably concord grape jelly (such as Concord® grape jelly). To mix with the other additives, the flavored jelly preferably has a consistency less than that found in the industry. The viscosity can be reduced by heating, beating, or otherwise thinning the jelly.

Another possible embodiment of the attracting agent comprises taking a liquid formed from grapes, preferably concord grapes. Optionally, the grape juice may be thickened so that it is capable of being spread without soaking into the ground soon thereafter. If the composition soaks into the ground it will pick up extra water, which can destroy the toxicity of the composition. Moreover, if the composition soaks into the ground, the composition will not be readily available to the fire ants and will not achieve its desired results. Because the composition can be used in ways other than spreading it on the ground (i.e. keeping the composition in a container and placing the container near the area to be treated), it is not critical that a thickening agent be added to the composition.

Thickening agents and methods to thicken liquid compositions are well known and need no detailed description here. The particular thickening agent and process to increase the viscosity of the attracting agent is not critical but merely must possess the property of increasing the viscosity to such an amount that after being spread it will not soon thereafter soak into the ground. To meet this property, the viscosity of the attracting agent may be increased to an amount greater than that of water (approximately 1 cp), and preferably greater than that of salad oil (approximately 30 cp).

An enhancing agent is added to the attracting agent. One possible embodiment of the enhancing agent is a salt at a concentration between approximately 2.4 weight percent and approximately 3.7 weight percent. This mixture forms a foul smelling gel that is distinct from the typical sweet odor of a flavored jelly or grape juice.

For purposes of the present invention, any edible salt, such as table salt, may be employed as the salt in the present invention. Examples of suitable edible salts include: organic acid salts, such as sodium citrate, sodium tartrate, sodium malate, sodium acetate, sodium lactate, and sodium succinate; phosphate salts such as sodium polyphosphate, sodium pyrophosphate, sodium metaphosphate, di- or tri-sodium phosphate, potassium polyphosphate, potassium pyrophosphate, potassium metaphosphate, and di or tri-potassium phosphate; carbonate salts such as sodium carbonate, sodium hydrogencarbonate, potassium carbonate, calcium carbonate, and magnesium carbonate; sulfate salts such as potassium sulfate, sodium sulfate, calcium sulfate, and magnesium sulfate; glutamates, such as monosodium glutamate; sodium chloride; calcium chloride; and potassium chloride.

A toxicant is additionally added to this mixture. The toxicant comprises an organophosphorous compound at a concentration between approximately 0.04 weight percent and approximately 1.2 weight percent. For purposes of the present invention, suitable organophosphorous compounds include phosphates, phosphoronionates, and phosphorothionates. For example, a suitable, well-known organophosphorous compounds, useful as toxicants in the present invention includes acetylphosphoramidithiotic acid O,S-dimethyl ester, more commonly called "Acephate," and commonly available under the "Ortho" and Orthene" brand names (see also U.S. Pat. Nos. 3,716,600 and 3,845,172, both assigned to Chevron).

Other examples of suitable organophosphorous compounds which have toxic effects toward fire ants, include, but are not limited to, phosphorothioic acid O,O-diethyl O-(3,5,6-trichloro-2-pyridinyl) ester, also known by "Chlorpyrifos", and commercially available under the "Dursban", "Lorsban", and "Pyrinex" brand names (see also U.S. Pat. No. 3,244,586 assigned to Dow Chemical); phosphorothioic acid O,O-diethyl O-[6-methyl-2-(1-methylethyl)-4-pyrimidinyl]ester, also known by "Dimpylate", and commercially available under the "Basudin", Diazinon", "Diazol", "Garden Tox", "Sarolex", and "Spectracide" brand names (see also U.S. Pat. No. 2,754,243 assigned to Geigy); phosphorothioic acid O,O-dimethyl O-(3-methyl-4-nitrophenyl) ester, also known by "Fenitrothion", and commercially available under the "Accothion", "Cyfen", "Cyten", "Folithion", "MEP", "Metathion" and "Sumithion" brand names (see also Belgian Pat. No. 594,669 to Sumitomo as well as Belgian Pat. No. 596,091 to Bayer); phosphorothioic acid O,O-dimethyl O-[3-methyl-4-(methylthio)phenyl]ester, also known by "Fenthion", and commercially available under the "Baycid", "Baytex", "Entex", "Lebaycid", "Mercaptophos", "Queletox", "Spotton", "Talodex" and "Tiguvon" brand names (see also German Patent No. 1,116,656 as well as U.S. Pat. No. 3,042,703, both assigned to Bayer; see also Japanese Pat. No. 15,130, which issued in 1964 to Sumitomo); 4-ethoxy-7-phenyl-3,5-dioxa-6-aza-4-phosphaoct-6-ene-8-nitrile 4-sulfide, also known by "Phoxim", and commercially available under the "Baythion", "Sebacil" and "Volaton" brand names (see also U.S. Pat. No. 3,591,662 assigned to Bayer); and the O,O-dimethyl analog of O-[2-(diethylamino)-6-methyl-4-pyrimidinyl]phosphorothioic acid O,O-diethyl ester, also known by "Pirimiphos-methyl", and commercially available under the "Actellic", "Blex", and "Silo San" brand names. (See, e.g., entry numbers 25, 2167, 2968, 3910, 3927, 7251 and 7372, respectively, in "The Merck Index", 10th ed., published in 1983 by Merck & Co., Inc.).

One feature of the present invention is that the composition has been observed to be attractive to fire ants while repulsive to most other ants, insects, rodents and other species. This, in addition to the low toxicant concentration, makes the toxicant environmentally safer than other prior art. The present invention is environmentally safe because (1) only a small percentage of the composition contains a toxicant that has already been approved by the EPA; (2) the composition does not appear to interfere with the ecological balance because it is repulsive to other species; and (3) the composition does not need to be used in great quantities because it appears to be highly attractive to fire ants.

Besides fire ants, the composition has been shown to attract and kill other hostile ants, roaches, bumble bees and some crickets. The composition does not attract and kill native bees, docile ants, mammals, birds, or other animals. If the enhancing agent is left out of the composition, not only will the fire ants no longer be as attracted to the composition, the composition will now attract and kill native bees, docile ants, mammals, and birds. Furthermore, the foul smell created by the addition of the enhancing agent, detracts people from tasting the composition. Without the attracting agent, the composition is sweet smelling and could accidently be consumed by people.

Additionally, because the composition can be utilized as a liquid or gel, it has the capacity to be spread in numerous ways, which include both air and land dispersal. The invention will also be able to be applied in a variety of void spaces including cracks and crevices, beneath doors and around windows, and in pipes, drains, and other conduits.

An unforeseen result in this combination is that the toxicant, when combined with the flavored jelly or grape juice, will remain toxic for an extended period. For example, organophosphorous compounds, such as Orthene, cannot be spread on concord grapes because the concord grapes would retain the organophosphorous compound. Such grapes would not be fit for consumption and cannot be used to make wine.

Another unforeseen result is that, after 60 days the mixed toxicant is no longer perceptible in the composition; however, the composition maintains its toxicity and will continue to kill fire ants. The level of citric acid of the composition also noticeably increases after 60 days.

The present invention will hereunder be described in even greater detail by reference to the following Examples, which are given here for illustrative purposes only and are by no means intended to limit the scope of the present invention.

A large scale ant farm was built to determine the ants' migration and hibernation habits. It was determined that the ants would not probe the surface for food unless the ground temperature was 50° F. at a depth of four inches. As the temperature was physically changed, the fire ants moved their larvae into different chambers throughout the nest.

EXAMPLE 1

Two pounds of grape jelly were heated to enable one-half teaspoon of Orthene to be mixed evenly throughout. These components were well mixed and then allowed to cool. Capsules were filled with the jelly-Orthene composition and placed on a fire ant bed. The fire ants were unable to penetrate the capsules.

The capsules were then manually opened and the jelly-Orthene composition was spread on the ground. The fire ants began feeding on the composition and there were numerous dead fire ants within a 24-hour period.

EXAMPLE 2

A similar composition as in Example 1 was used except that the concentration of the Orthene was gradually increased. The process entailed placing a high concentration of jelly-Orthene out for a short period and watching the way the fire ants fed on the composition. The sample was then removed and a low Orthene concentration was substituted. After the fire ants returned to their normal feeding habits, a sample with a higher Orthene concentration than previously used was tested. From this procedure, it was discovered that the fire ants would avoid the jelly-Orthene composition when the composition contained greater than 12 weight percent of Orthene.

EXAMPLE 3

Two pounds of grape jelly were heated to easily mix two tablespoons of table salt into solution. This compound formed a foul smelling substance and did not emit the typical sweet smell normally associated with jelly. Moreover, the compound no longer had a sweet taste but, rather, had a very bad taste. This salted-jelly was placed on a fire ant mound, and, immediately, the fire ants attacked this food source.

EXAMPLE 4

Two pounds of grape jelly was heated to easily mix one tablespoon of salt in solution. The compound formed a foul smelling substance similar to Example 3. This compound was placed on a fire ant mound, and the fire ants attacked this food source. The compound's attraction to fire ants was apparent but was not as immediate as Example 3.

EXAMPLE 5

A composition as described in Example 3 was tested against ordinary grape jelly. A sample of grape jelly was placed on the fire ant mound and was ultimately covered with fire ants. A sample of salted-jelly was then placed on the same mound, and the fire ants immediately left the first sample (salt-free jelly) and consumed the salted-jelly.

EXAMPLE 6

A sample was prepared by heating two pounds of grape jelly and mixing two tablespoons of table salt and a half a tablespoon of Orthene. One drop of the composition was placed in a vegetable garden in the middle of the rows every two to three feet. All fire ant mounds in the garden, as well as the fire ant mounds within 50 feet of the garden, were killed.

EXAMPLE 7

A few drops of the composition as described in Example 6 was placed on small pieces of cardboard and placed on fire ant trails located inside several houses. Within 12 hours the fire ants were no longer found within the houses, and typically a mound near each house was found soon thereafter with dead fire ants.

EXAMPLE 8

The purpose of this Example was to show that the composition does not attract ants other than aggressive ants. A sample was prepared by heating two pounds of grape jelly and mixing two tablespoons of table salt and a half a tablespoon of Orthene. This composition was placed on three separate ant hills. The first ant hill was a Native Ant, Harvester, or Red Ant mound in which the ants were highly aggressive. The sample was placed on this first mound, and the ants immediately began to consume the composition. Within 24 hours, the first bed was covered with dead ants. There were no ants left on the first mound.

The second ant hill was a combination of ants with both aggressive and docile traits. The sample was placed on this mound, and the same proportion of aggressive ants immediately began to consume the composition. Within 24 hours, a portion of the ants were dead. A determination was made and it appeared that only the docile ants survived.

The last ant hill was a mound of docile ants. The sample was then placed on the mound and only a few ants began to consume the composition. Within 24 hours, only a negligible number of ants were dead.

EXAMPLE 9

The purpose of this Example was to show that the composition does not attract mammals. A sample was prepared by heating two pounds of grape jelly and mixing two tablespoons of table salt and a half a tablespoon of Orthene. This composition was placed in dog food pans and placed within yards located on several different farms. Dogs, as well as other mammals, located on the yard would not eat the composition at all. The dog food pans containing the composition were also placed in yards that were remote from areas infested with fire ants. The composition was undisturbed by both ants and mammals.

EXAMPLE 10

The purpose of this Example was to show that the composition does not attract honey bees. Over a two year period, the composition of Example 9 was placed on the ground around a honey bee hive and around the entrance to the hive. Fire ants, which had infested the area, did not infest the hive. The honey bees went around the composition and did not eat it.

EXAMPLE 11

The purpose of this Example was to show that the composition does not attract birds. Killdeers nest on the ground and fire ants typically eat their eggs. Over a two year period, the composition of Example 9 was placed around the nests of killdeers located on a farm infested with fire ants. The killdeers did not consume the composition. Over the two year period, the number of killdeers on this farm increased at least 10-fold.

EXAMPLE 12

A sample was prepared by heating two pounds of grape jelly and mixing two tablespoons of table salt and a half a tablespoon of Orthene. This composition was placed 400 feet from a large nest of fire ants. After three days there were no perceptible dead ants. The sample was then moved 10 feet closer, and the nest was watched for another three days. By this method, it was determined that the ants would travel 200 feet from their mound to reach the bait.

EXAMPLE 13

A sample was prepared by heating two pounds of grape jelly and mixing two tablespoons of table salt and a half a tablespoon of Orthene. The composition was tested in cold weather, and the composition would kill 100 percent of the fire ant mounds located within 3 feet of the sample.

EXAMPLE 14

The composition was prepared by heating grape jelly and mixing it in a ratio of two pounds of grape jelly to two tablespoons of table salt to a half a tablespoon of Orthene. The composition was blown high into the air and let fall back to the ground. Approximately one quart of the composition was required per acre of land with a high density of fire ant mounds to ensure 100 percent kill of the mounds.

EXAMPLE 15

A sample was prepared by heating two pounds of concord grape jelly and mixing two tablespoons of table salt and a half a tablespoon of Orthene. Once exposed to the elements, the sample remains active 30 to 60 days if there was not any heavy rain or heavy dew.

EXAMPLE 16

A sample was prepared by heating two pounds of concord grape jelly and mixing two tablespoons of table salt and a half a tablespoon of Orthene. The sample was kept in a container, and after 60 days the sample was tested for chemical composition. The level of citric acid in the composition had noticeably risen, and there was no perceptible trace of the Orthene in the composition. This composition was then placed near several fire ant mounds. The fire ant mounds were later found dead.

EXAMPLE 17

A sample was prepared by whipping eight fluid ounces of grape juice and one cup of flour into a thick mixture. The mixture was then further mixed with one-half a tablespoon of table salt and a quarter of a tablespoon of Orthene. This composition was then placed near several fire ant mounds. The fire ants at these mounds were later found dead.

While the preferred embodiments of the present invention and their advantages have been disclosed in the above detailed description, the invention is not limited thereto, but only by the spirit and scope of the appended claims.

What is claimed is:

1. A bait composition for exterminating insects formed by a method comprising:

selecting an attracting agent comprised of concord grape extract;

selecting a salt to enhance the attractability of the attracting agent to insects, said salt being an edible salt chosen from the group consisting of an organic acid salt, a phosphate salt, a carbonate salt, a sulfate salt, a glutmate, calcium chloride, potassium chloride, table salt, and combinations thereof;

selecting a toxicant comprised of an organophosphorous compound; and mixing said attracting agent, said salt, and said toxicant, such that said salt is at least about 2.4 weight percent of the pre-mixed total weight of said attracting agent, said salt, and said toxicant, and said toxicant is at least about 0.04 weight percent of said pre-mixed total weight.

2. The composition as defined in claim 1, wherein said salt is comprised of table salt.

3. The composition as defined in claim 1, wherein said salt is an edible salt chosen from the group consisting of an organic acid salt, a phosphate salt, a carbonate salt, a sulfate salt, a glutmate, calcium chloride, potassium chloride, and combinations thereof.

4. The composition as defined in claim 2, wherein said salt is at most about 3.7 weight percent of said pre-mixed total weight.

5. The composition as defined in claim 3, wherein said salt is at most about 3.7 weight percent of said pre-mixed total weight.

6. The composition as defined in claim 1, wherein said toxicant is comprised of acetylphosphoramidothiotic acid O,S-dimethyl ester.

7. The composition as defined in claim 1, wherein said toxicant is at most about 1.2 weight percent of said pre-mixed total weight.

8. A bait composition for exterminating insects formed by a method comprising:

selecting an attracting agent comprised of concord grape extract;

selecting a salt to enhance the attractability of the attracting agent to insects, said salt being an edible salt chosen from the group consisting of an organic acid salt, a phosphate salt, a carbonate salt, a sulfate salt, a glutamate, calcium chloride, potassium chloride, table salt, and combinations thereof;

selecting a toxicant comprised of an organophosphorous compound; and mixing said attracting agent, said salt, and said toxicant such that the pre-mixed ratio of said salt to said attracting agent is at least about one-half tablespoon of said salt to eight fluid ounces of said attracting agent, and the premixed ratio of said toxicant to said attracting agent is at least about one-quarter tablespoon of said toxicant to eight fluid ounces of said attracting agent.

9. The composition as defined in claim 8, wherein said salt is comprised of table salt.

10. The composition as defined in claim 8, wherein said salt is an edible salt chosen from the group consisting of an organic acid salt, a phosphate salt, a carbonate salt, a sulfate salt, a glutamate, calcium chloride, potassium chloride, and combinations thereof.

11. The composition as defined in claim 8, wherein said organophosphorous compound is comprised of acetylphosphoramidothiotic acid O,S-dimethyl ester.

12. The composition as defined in claim 8, wherein said salt is comprised of table salt; and said toxicant is comprised of acetylphosphoramidothiotic acid O,S-dimethyl ester.

13. The composition as defined in claim 8, wherein said salt is an edible salt chosen from the group consisting of an organic acid salt, a phosphate salt, a carbonate salt, a sulfate salt, a glutmate, calcium chloride, potassium chloride, and combinations thereof; and said toxicant is comprised of acetylphosphoramidothiotic acid O,S-dimethyl ester.

14. A bait composition for exterminating insects formed by a method comprising:

selecting an attracting agent comprised of concord grape jelly;

selecting a salt to enhance the attractability of the attracting agent to insects, said salt being an edible salt chosen from the group consisting of an organic acid salt, a phosphate salt, a carbonate salt, a sulfate salt, a glutamate, calcium chloride, potassium chloride, table salt, and combinations thereof;

selecting a toxicant comprised of an organophosphorous compound; and mixing said attracting agent, said salt, and said toxicant, such that said salt is at least about 2.4 weight percent of the pre-mixed total weight of said attracting agent, said salt, and said toxicant, and said toxicant is at least about 0.04 weight percent of said pre-mixed total weight.

15. The composition as defined in claim 14, wherein said salt is comprised of table salt.

16. The composition as defined in claim 14, wherein said salt is an edible salt chosen from the group consisting of an organic acid salt, a phosphate salt, a carbonate salt, a sulfate salt, a glutamate, calcium chloride, potassium chloride, and combinations thereof.

17. The composition as defined in claim 14, wherein said toxicant is comprised of acetylphosphoramidothiotic acid O,S-dimethyl ester.

18. The composition as defined in claim 1, wherein said salt is comprised of table salt;

said toxicant is comprised of acetylphosphoramidothiotic acid O,S-dimethyl ester; and said salt is at most about 3.7 weight percent of said pre-mixed total weight, and said toxicant is at most about 1.2 weight percent of said pre-mixed total weight.

19. The composition as defined in claim 1, wherein said salt is an edible salt chosen from the group consisting of an organic acid salt, a phosphate salt, a carbonate salt, a sulfate salt, a glutamate, calcium chloride, potassium chloride, and combinations thereof;

said toxicant is comprised of acetylphosphoramidothiotic acid O,S-dimethyl ester; and said salt is at most about 3.7 weight percent of said pre-mixed total weight, and said toxicant is at most about 1.2 weight percent of said pre-mixed total weight.

20. The composition as defined in claim 15, wherein said salt is at most about 3.7 weight percent of said pre-mixed total weight.

21. The composition as defined in claim 16, wherein said salt is at most about 3.7 weight percent of said pre-mixed total weight.

22. The composition as defined in claim 14, wherein said toxicant is at most about 1.2 weight percent of said pre-mixed total weight.

23. The composition as defined in claim 14, wherein
said salt is comprised of table salt;
said toxicant is comprised of acetylphosphoramidothiotic acid O,S-dimethyl ester; and
said salt is at most about 3.7 weight percent of said mixture, and said toxicant is at most about 1.2 weight percent of said pre-mixed total weight.

24. The composition as defined in claim 14, wherein
said salt is an edible salt chosen from the group consisting of an organic acid salt, a phosphate salt, a carbonate salt, a sulfate salt, a glutamate, calcium chloride, potassium chloride, and combinations thereof;
said toxicant is comprised of acetylphosphoramidothiotic acid O,S-dimethyl ester; and
said salt is at most about 3.7 weight percent of said pre-mixed total weight, and said toxicant is at most about 1.2 weight percent of said pre-mixed total weight.

25. A bait composition for exterminating insects formed by a method comprising:
selecting a concord grape jelly;
selecting a salt to enhance the attractability of the concord grape jelly to insects, said salt being an edible salt chosen from the group consisting of an organic acid salt, a phosphate salt, a carbonate salt, a sulfate salt, a glutamate, calcium chloride, potassium chloride, table salt, and combinations thereof;
selecting an organophosphorous compound; and
mixing said concord grape jelly, said salt, and said organophosphorous compound such that
the pre-mixed ratio of said salt to said concord grape jelly is at least about one tablespoon of said salt to two pounds of concord grape jelly, and
the pre-mixed ratio of said organophosphorous compound to said concord grape jelly is at least about one half teaspoon of said organophosphorous compound to two pounds of concord grape jelly.

26. The composition as defined in claim 25, wherein said salt is comprised of table salt.

27. The composition as defined in claim 25, wherein said salt is an edible salt chosen from the group consisting of an organic acid salt, a phosphate salt, a carbonate salt, a sulfate salt, a glutamate, calcium chloride, potassium chloride, and combinations thereof.

28. The composition as defined in claim 25, wherein said organophosphorous compound is comprised of acetylphosphoramidothiotic acid O,S-dimethyl ester.

29. The composition as defined in claim 25, wherein
said salt is comprised of table salt; and
said organophosphorous compound is comprised of acetylphosphoramidothiotic acid O,S-dimethyl ester.

30. The composition as defined in claim 25, wherein
said salt is an edible salt chosen from the group consisting of an organic acid salt, a phosphate salt, a carbonate salt, a sulfate salt, a glutamate, calcium chloride, potassium chloride, and combinations thereof; and
said organophosphorous compound is comprised of acetylphosphoramidothiotic acid O,S-dimethyl ester.

31. The composition as defined in claim 25, wherein
the premixed ratio of said salt to the concord grape jelly is at least about two tablespoons of said salt to two pounds of concord grape jelly, and
the pre-mixed ratio of said organophosphorous compound to said concord grape jelly is at least about one-half tablespoon of said organophosphorous compound to two pounds of concord grape jelly.

32. The composition as defined in claim 31, wherein said salt is comprised of table salt.

33. The composition as defined in claim 31, wherein said salt an edible salt chosen from the group consisting of an organic acid salt, a phosphate salt, a carbonate salt, a sulfate salt, a glutamate, calcium chloride, potassium chloride, and combinations thereof.

34. The composition as defined in claim 31, wherein said organophosphorous compound is comprised of acetylphosphoramidothiotic acid O,S-dimethyl ester.

35. The composition as defined in claim 31, wherein
said salt is comprised of table salt; and
said organophosphorous compound is comprised of acetylphosphoramidothiotic acid O,S-dimethyl ester.

36. The composition as defined in claim 31, wherein
said salt is an edible salt chosen from the group consisting of an organic acid salt, a phosphate salt, a carbonate salt, a sulfate salt, a glutamate, calcium chloride, potassium chloride, and combinations thereof; and
said organophosphorous compound is comprised of acetylphosphoramidothiotic acid O,S-dimethyl ester.

* * * * *